(12) United States Patent
Frederix et al.

(10) Patent No.: US 11,486,851 B2
(45) Date of Patent: Nov. 1, 2022

(54) ELECTROCHEMICAL GAS SENSORS

(71) Applicant: ams AG, Premstaetten (AT)

(72) Inventors: Filip Frederix, Diest (BE); Erik Jan Lous, Veldhoven (NL)

(73) Assignee: ams AG, Premstaetten (AT)

( * ) Notice: Subject to any disclaimer, the term of this patent is extended or adjusted under 35 U.S.C. 154(b) by 0 days.

(21) Appl. No.: 16/134,154

(22) Filed: Sep. 18, 2018

(65) Prior Publication Data

US 2020/0088672 A1  Mar. 19, 2020

(51) Int. Cl.
*G01N 27/407* (2006.01)

(52) U.S. Cl.
CPC .................. *G01N 27/407* (2013.01)

(58) Field of Classification Search
CPC ............. G01N 27/407; G01N 33/4074; G01N 27/4074; G01N 33/4972
See application file for complete search history.

(56) References Cited

U.S. PATENT DOCUMENTS

| | | | | |
|---|---|---|---|---|
| 6,103,080 A * | 8/2000 | Pham | ...................... | F01N 11/00 204/424 |
| 7,045,047 B2 * | 5/2006 | Nakae | ................. | G01N 27/4074 204/402 |
| 7,306,712 B2 * | 12/2007 | Watanabe | ............ | G01N 33/005 205/784 |
| 7,770,432 B2 * | 8/2010 | Roesch | .............. | G01N 15/0656 73/23.33 |
| 8,820,140 B2 * | 9/2014 | Puget | ..................... | G01N 30/78 73/23.39 |
| 9,395,324 B2 * | 7/2016 | Zribi | .................. | G01N 27/4074 |
| 9,746,439 B2 * | 8/2017 | Porro | ................. | G01N 33/0027 |
| 2004/0086768 A1 | 5/2004 | Fleckner et al. | | |
| 2005/0214169 A1 | 9/2005 | Leddy et al. | | |
| 2007/0289870 A1* | 12/2007 | Nair | .................... | G01N 27/4062 204/424 |
| 2015/0360936 A1* | 12/2015 | Tayebi | ................. | B81C 1/0023 257/369 |
| 2016/0047774 A1* | 2/2016 | Teysseyre | .......... | G01N 27/4065 205/775 |
| 2016/0146752 A1 | 5/2016 | Roelver et al. | | |
| 2016/0290946 A1* | 10/2016 | Montanya Silvestre | ..................... G01N 33/0027 | |
| 2017/0199147 A1* | 7/2017 | Pruitt | ..................... | G01N 27/49 |

(Continued)

FOREIGN PATENT DOCUMENTS

WO    2017118490 A1    7/2017

OTHER PUBLICATIONS

A.C. Fischer, Integrating MEMS and ICs, Microsystems & Nanoengineering, 2015, 15005, p. 1-16. (Year: 2015).*

(Continued)

*Primary Examiner* — Luan V Van
*Assistant Examiner* — Caitlyn Mingyun Sun
(74) *Attorney, Agent, or Firm* — Kilpatrick Townsend & Stockton LLP (57) ABSTRACT

A gas sensor comprises an electrochemical film, a plurality of electrodes coupled with the electrochemical film and a semiconductor wafer coupled with the plurality of electrodes. A passivation layer is formed between the electrochemical firm and the semiconductor wafer and a dielectric layer is coupled between the electrochemical film and the semiconductor wafer.

8 Claims, 10 Drawing Sheets

(56) References Cited

U.S. PATENT DOCUMENTS

2017/0322173 A1    11/2017    Widenmeyer et al.

OTHER PUBLICATIONS

H.K. Gatty, A wafer-level liquid cavity integrated amperometric gas sensor with ppb-level nitric oxide gas sensitivity, J. Micromech. Microeng. 2015(25), 105013, p. 1-10. (Year: 2015).*

A Thesis Presented to The Graduate Faculty of The University of Akron, article entitled: "Low Catalyst Loaded Ethanol Gas Fuel Cell Sensor," by Amir Amirfazli, dated Aug. 2017 in 74 pages.

Doctoral Thesis by Hithesh Kumar Gatty, article entitled: "MEMS-based electrochemical gas sensors and wafer-level methods," KTH Electrical Engineering, Tryck: Universitetsservice US AB, Stockholm 2015, dated Oct. 2015 in 91 pages.

Kazuhiro Kamiya, and Masao Sudoh, article entitled: "Response characteristics of fuel cell type alcohol sensor using Nafion membrane," Department of Materials Science and Chemical Engineering, Shizuoka University 3-5-1 Johoku, Hamamatsu, Shizuoka 432-8561, Japan, Abstract #2635, 224th ECS Meeting, © 2013 The Electrochemical Society in 1 page.

PCT/EP2019/075076 International Search Report and Written Opinion, dated Nov. 29, 2019.

Ranjan I L S et al: 11 "Compact and flexible hydrocarbon polymer sensor for sensing humidity in confined spaces" 11 ,International Journal of Hydrogen Energy, Elsevier Science Publishers B.V., Barking,GB,vol. 39, No. 36, Nov. 7, 2014 (Nov. 7, 2014), pp. 21343-21350, XP029096656, ISSN: 0360-3199, DOI: 10.1016/J. IJHYDENE.2014.10.085.

* cited by examiner

STATE OF THE ART

Figure 1

STATE OF THE ART

Process Integration flow (1)

Process Integration flow (3)

ELECTROCHEMICAL GAS SENSORS

FIELD

The disclosure relates to gas sensors, particularly but not exclusively, to electrochemical alcohol sensors.

BACKGROUND

Law enforcement agencies use electrochemical fuel cell sensors as these sensors show an increased accuracy and reliability compared to current semiconductor based metal oxide (MOx) sensors. However, these sensors are large which makes it difficult to integrate them into a mobile phone.

Electrochemical alcohol fuel cell sensors have already several advantages compared to existing sensor methodologies. Current electrochemical sensors or fuel cell sensors have low power consumption, very good sensitivity, specificity and response time. Because of their high accuracy, they are used by law enforcement agencies. However, they are currently still too expensive and too large to be used in for example a mobile phone. There is currently no sensor which is small, accurate, low power, and cost-effective enough to be used in consumer applications. Examples of electrochemical fuel sensors can be found in US 2013/0277217, US 2016/0146752, US 2004/0086768, US 2017/0322173, "MEMS-based electrochemical gas sensors and wafer-level methods" by Hithesh Kumar Gatty and "Response Characteristics of Fuel Cell Type Alcohol Sensor Using Nafion Membrane" by Kazuhiro Kamiyaa and Masao Sudoha.

There are other different sensor methodologies used to make an alcohol breath analysing device. The most commonly known sensor principles are the MOx or MOS sensors (Metal Oxide Sensors) and the IR (Infra-Red) sensors.

IR sensors have a better sensitivity and specificity but are very large and very expensive. It is difficult to miniaturize IR sensors.

MOx sensors are also made via standard semiconductor processes, which makes them less expensive compared to the more accurate electrochemical fuel cell sensors. MOx sensors have a small footprint, are inexpensive, but require higher temperatures and consume too much power to be used in consumer applications such as, for example, in a mobile phone. Furthermore, they are not very sensitive, not specific, and are prone to false positives. The performance is therefore not good enough for a reliable and accurate sensor in a consumer device such as a mobile phone. It is difficult to make MOx sensors low power or give them a better specificity.

An electrochemical fuel cell sensor can be compared to a battery. While a battery constantly delivers a voltage output, a fuel cell sensor only delivers a voltage output when alcohol is injected into the sensor. The output voltage is very small (in the low millivolts) and is linear to the alcohol level present and being measured. The output voltage is generated via an electro-chemical reaction that occurs when alcohol is applied to the fuel cell electrolyte solution, this reaction will only last for a short time (and is dependent on alcohol concentration level) upon which the output will then dissipate back to zero voltage.

Figure 1:
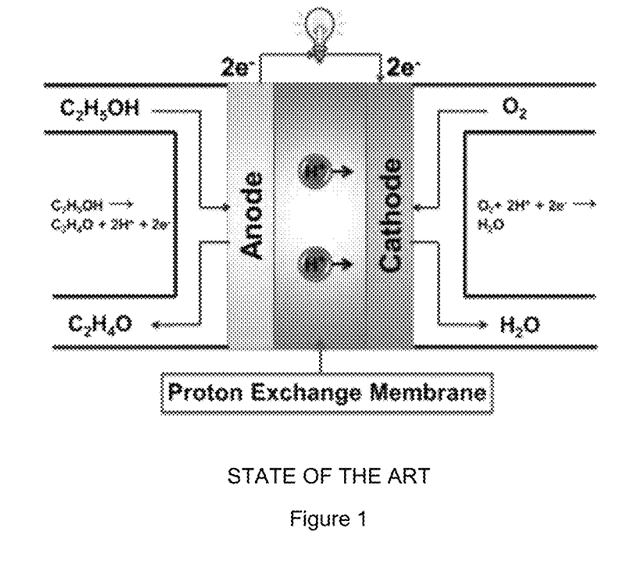
FIG. 1 shows a schematic illustration of an electrochemical reaction across a proton exchange membrane according to the state-of-the-art.
Figure 2:
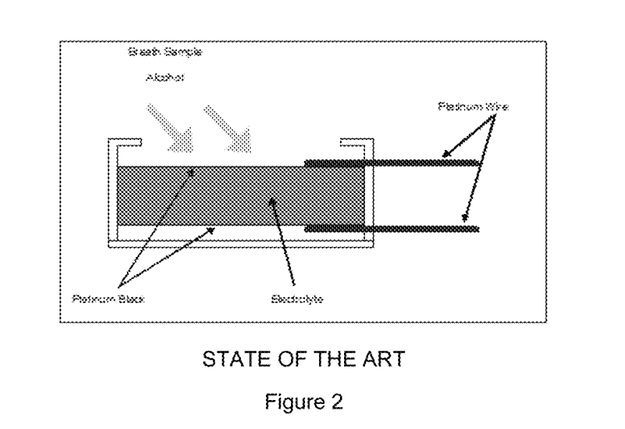
FIG. 2 illustrates an electrochemical fuel cell gas sensor according to the state-of-the-art.

An electrochemical reaction for ethanol in an alcohol sensor, across a proton exchange membrane is shown in FIG. 1. An example of the core of current electrochemical fuel cell sensors is shown in FIG. 2. Solid electrolytes are available and can be used for alcohol detection as shown in Amirfazli, Amir "Low Catalyst Loaded Ethanol Gas Fuel Cell Sensor." Electronic Thesis or Dissertation. University of Akron, 2017.

SUMMARY

This disclosure relates to electrochemical fuel cell alcohol sensors realized via standard semiconductor processes. The sensors could be used for the detection of, for example, alcohol in a breath analysis. The sensors may be used where breath sensors are currently not used, such as mobile phones.

Compared to standard state-of-the-art alcohol sensors, the device disclosed is in general a more accurate, cost effective, and smaller sensor device.

These features are important for integrating a sensor in a mobile phone or in consumer devices or handheld devices in general. The current existing sensor solutions are too bulky and too expensive or they are not accurate enough.

Semiconductor processes have the ability to shrink sensor technologies and, at high volumes, lower the cost per sensor. Therefore an electrochemical fuel cell alcohol sensor using semiconductor processes would provide a sensor which is accurate, small, inexpensive, and consume less power. Semiconductor-based electrochemical fuel cell sensors can therefore be used as accurate sensors in a mobile phone, consumer reader devices, or other handheld or consumer devices.

Producing electrochemical fuel cell sensors with semiconductor processes should overcome the drawbacks of current electrochemical fuel cell sensors described above of large cost and large sensor footprint.

Realizing an electrochemical fuel cell sensor with a semiconductor process has several advantages compared to existing solutions, such as accuracy, size, and cost. Preferably, solid electrolytes may be used and vias or open structures in the chip architecture may be created.

The gas sensor may be monolithically integrated into a semiconductor circuit, such as an ASIC. This has clear advantages in performance, for example, low noise, response time, cost, and power. Combining application specific integrated circuit (ASIC) and microelectromechanical systems (MEMS) processing in one flow and one process is advantageous over conventional electrochemical sensors such as alcohol sensors. The use of an ASIC allows read out and detection of a current/voltage digital signal from the fuel cell sensor. An ASIC can be manufactured very close to the electrochemical fuel cell which allows low capacitance, low resistances, and low noise. The ASIC has a high sensitivity and can be used to count single protons from the electrochemical fuel cell. Calculation and processing as well as calibration can also be performed on the ASIC.

The gas sensor proposed in the present disclosure has in general the following advantages over current state-of-the-art devices:
  better accuracy;
  lower noise;
  smaller size;
  lower power; and
  smaller form factor.

The electrochemical fuel cell sensor could be used for alcohol detection, but also other analytes could be detected. Other electrolyte materials or sensor settings may be used to detect other analytes. It will be appreciated that the applications go beyond alcohol sensing.

According to one aspect of the present disclosure, there is provided a gas sensor comprising: an electrochemical film;

a plurality of electrodes coupled with the electrochemical film; and a semiconductor wafer coupled with the plurality of electrodes.

Advantageously, the semiconductor wafer may be an application specific integrated circuit complementary metal oxide semiconductor (ASIC CMOS) wafer. Integration of the sensor on top of an ASIC gives reduced (or lowest possible) cost, power, and form factor.

The gas sensor may be monolithically integrated on to the ASIC CMOS wafer. Advantageously, this ensures shortest lead/connection lines to the sensor and therefore ensures lowest noise levels and lowest parasitic capacitance, resulting in improved (or best) sensor speed performance. The use of an ASIC allows a high sensitivity gas sensor.

Advantageously, the gas sensor may be formed using a semiconductor process. This reduces the manufacturing cost of the sensor.

The gas sensor may further comprise a dielectric layer coupled between the electrochemical film and the semiconductor wafer, and the dielectric layer may comprise an etched cavity portion. The cavity allows gas to pass through the electrolyte and escape from the sides of the sensor chip.

The ASIC wafer may comprise laterally spaced structures having holes between them. These holes allow the gas to be sensed to pass through the sensor chip.

The ASIC wafer may extend under an entire area of the electrochemical film. In other words, the ASIC wafer may extend in two directions underneath the electrochemical film and the electrochemical film may be laid on top of the wafer, parallel to the wafer. Conveniently, this further reduces the distance between the electrodes and the wafer.

The gas sensor may further comprise a passivation layer between the electrochemical film and the semiconductor wafer. The passivation layer protects the underlying ASIC on the semiconductor wafer. The quality of the ASIC is therefore unaffected by atmospheric gases or relative humidity.

The gas sensor may be configured such that the gas to be sensed passes in a lateral direction through the electrochemical film. This does not require the gas to be measured to pass through the electrolyte. All of the plurality of electrical electrodes may be formed on a single surface of the electrochemical film. This geometry makes the semiconductor processing of the fuel cell easier.

At least some of the plurality of electrodes may be located on a first surface of the electrochemical film, and at least some of the plurality of electrodes may be located on a second surface of the electrochemical film, and wherein the first surface of the electrochemical film and the second surface of the electrochemical film are opposite surfaces.

The gas sensor may be configured such that the gas to be sensed passes through the electrochemical film in a transverse direction from the first surface to the second surface.

Each of at least some of the plurality of electrodes, located on either the first surface or second surface, may extend between the electrochemical film and the semiconductor wafer. In other words, the height of the electrodes on the bottom surface of the electrochemical film may be increased. This provides support for the Nafion film. Alternatively, the heights of the electrodes and the cavity height may be decreased.

The plurality of electrodes may form a comb or meander structure. This increases the surface area of the electrodes, to improve detection of the analyte.

The gas sensor may be configured to be an alcohol sensor.

The electrochemical film may be a solid electrolyte. Advantageously, this makes the semiconductor processing of the sensor easier. This allows a simpler device as the electrochemical film does not have to be constrained.

The gas sensor may further comprise through silicon holes, through which the gas may enter and/or escape. These are unfilled through silicon vias.

The gas sensor may further comprise through passivation via-connections connecting the semiconductor wafer with at least some of the plurality of electrodes.

In use, the electrochemical film and the plurality of electrodes may form an electrochemical fuel cell.

According to a further aspect of the present disclosure, there is provided a method of manufacturing a gas sensing device. The method comprises: forming an electrochemical film; forming a plurality of electrodes coupled with the electrochemical film; and forming a semiconductor wafer coupled with the electrodes.

To better understand the nature and advantages of the present disclosure, reference should be made to the following description and the accompanying figures. It is to be understood, however, that each of the figures is provided for the purpose of illustration only and is not intended as a definition of the limits of the scope of the present disclosure. Also, as a general rule, and unless it is evident to the contrary from the description, where elements in different figures use identical reference numbers, the elements are generally either identical or at least similar in function or purpose.

BRIEF DESCRIPTION OF THE DRAWINGS

Some preferred embodiments of the disclosure will now be disclosed by way of example only and with reference to the accompanying drawings, in which.

DETAILED DESCRIPTION

Figure 3:
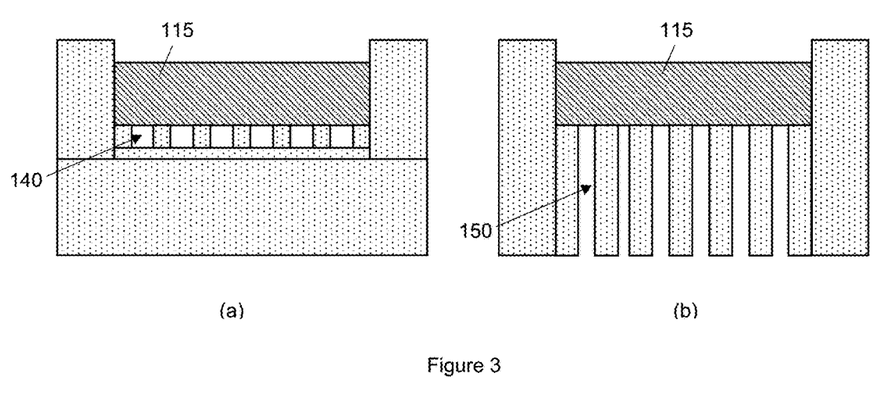
FIG. 3 illustrates a cross-sectional view of gas sensor structures according to the present disclosure.

FIG. 3 illustrates a cross-sectional view of gas sensor structures according to the present disclosure. When integrating an electrochemical fuel cell sensor into a semiconductor chip, it is desirable for the gas to be measured to go through the electrolyte.

This is provided by the form factors shown in FIG. 3. The structure of FIG. 3(a) has some open structures or cavities 140 underneath the electrolyte 115 so that the gas can pass through the electrolyte 115 and can escape at the sides of the sensor chip. The structure of FIG. 3(b) has through silicon holes 150 which allow the gas to pass through the chip. Alternatively, the holes 150 may be one or more larger openings.

Figure 4:
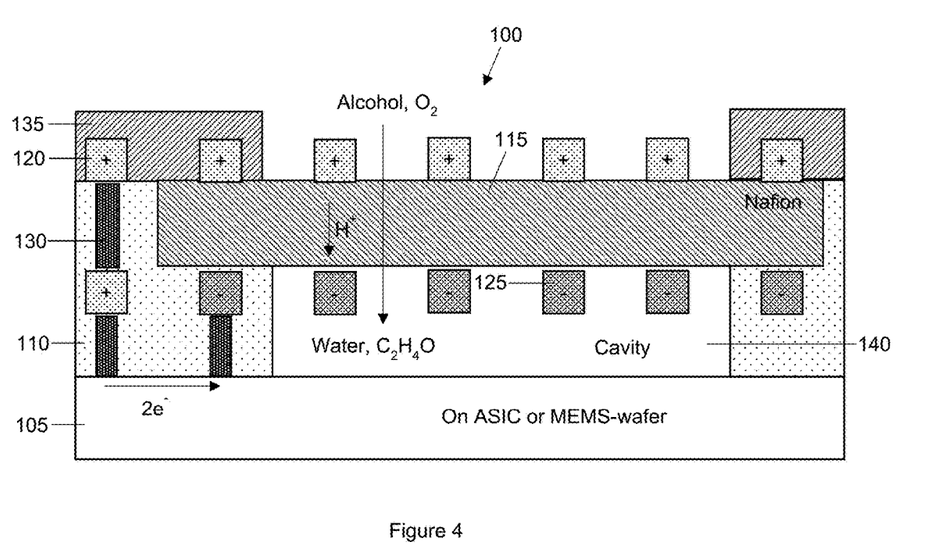
FIG. 4 illustrates a cross-sectional view of a gas sensor according to one embodiment of the present disclosure.

FIG. 4 illustrates a cross-sectional view of a gas sensor according to one embodiment of the present disclosure. The gas sensor 100 comprises an electrochemical film 115 supported by a CMOS backend metallization stack or dielectric layer 110. The dielectric layer 110 is etched to form a cavity 140. The cavity 140 allows gas to pass through the electrolyte and leave the sensor at the sides of the chip. The dielectric layer 110 is formed on top of a wafer 105. This wafer 105 can be either a MEMS-wafer or an ASIC wafer. A passivation layer (not shown) forms part of the ASIC wafer 105, and the dielectric layer 110 is formed on the passivation layer. In this example, the electrochemical film 115 is directly accessible on both sides by the air flow from breath. The electrochemical film 115 is sandwiched in between first (positive) electrodes 120 and second (negative) electrodes 125. These electrodes 120, 125 provide support to the electrochemical film 115. However, further structures may also provide support (not shown) as necessary.

In this embodiment with a cavity 140, the analyte (ethanol) penetrates through the proton carrying film (Nafion) 115. The electrochemical film 115, used to support the electrochemical reaction of alcohol in the sensor is Nafion. Nafion has improved thermal and mechanical stability. As a film, Nafion™ perfluorosulfonic acid (PFSA) membranes are non-reinforced films based on chemically stabilized PFSA/polytetrafluoroethylene (PTFE) copolymer in the acid (H+) form. As it is close to Teflon (backbone), it is seen as compatible with semiconductor processing.

Other alternatives to Nafion may be used. These include hydrocarbon backbones, composite membranes (including grafted membranes, organic and inorganic nanocomposites, and Nafion based composites) and blended membranes. For example, other solid electrolytes that could be used include yttria-stabilized zirconia, beta-alumina, fluoride ion conductors such as lanthanum trifluoride, iodides such as silver iodide, silver sulfide, lead(II) chloride, perovskite ceramics such as strontium titanate and strontium stannate, polyacrylamides and agar, among others.

The sensor is monolithically integrated on top of an ASIC 105. This brings shortest lead/connection lines to the sensor and therefore gives lowest noise-levels and lowest parasitic capacitance and resistances, resulting in best sensor speed performance. Integration on top of ASIC also gives lowest cost, power, and form factor.

The device has via connections or through passivation via-connections 130 formed through the inter-metal dielectric of the backend layers 110. These connect the electrodes 120, 125 to the ASIC wafer 105. A passivation layer 135 is formed over the sensor leaving the Nafion film 115 exposed to the outside environment, preferably where the electrodes are.

Figure 5:
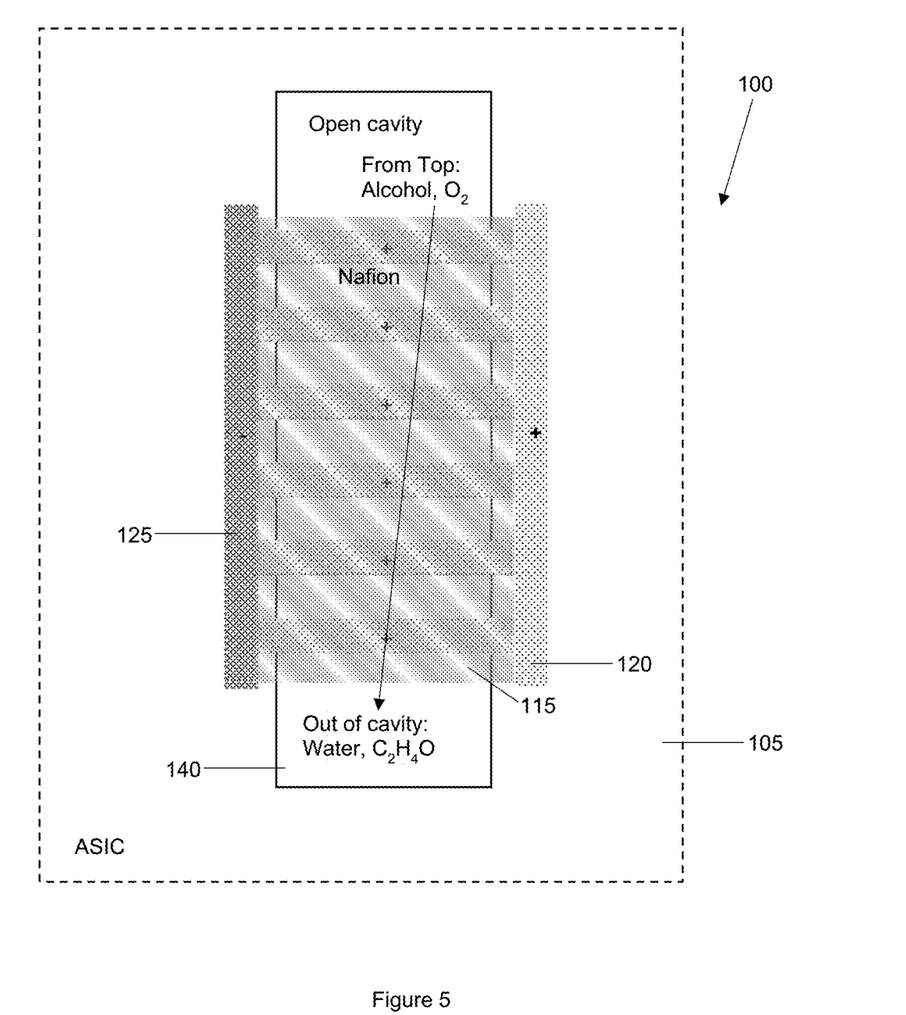
FIG. 5 illustrates a top view of a gas sensor according to one embodiment of the present disclosure.

FIG. 5 illustrates a top view of a gas sensor according to one embodiment on the present disclosure. Many of the features of FIG. 5 are the same as FIG. 4 and therefore carry the same reference numerals. The Nafion film 115 is formed across the cavity portion 140. In this example, the second (negative) electrodes 125 are formed below the Nafion film 115, and the first (positive) electrodes 120 are formed above the Nafion film 115. The second (negative) electrodes 125 are partially obscured in this view by the first (positive) electrodes 120. Gas (containing alcohol and oxygen) flows from above the Nafion film 115, reacts with the electrochemical film 115 to produce water and $C_2H_4O$ which then flows into the cavity, where it escapes the chip through any opening. This is then measured by the electrodes 120, 125.

Figure 6:
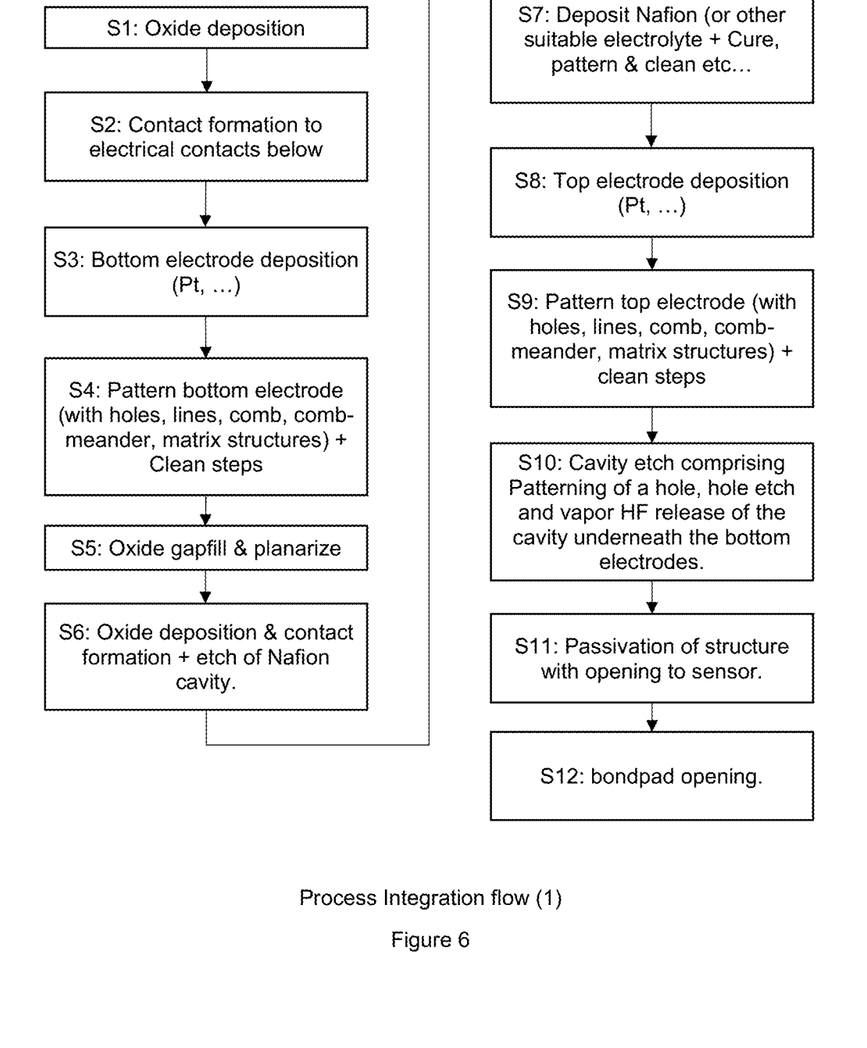
FIG. 6 illustrates an exemplary flow diagram outlining a manufacturing method of a gas sensor according to one embodiment of the present disclosure.

FIG. 6 illustrates an exemplary flow diagram outlining a manufacturing method of a gas sensor according to one embodiment of the present disclosure, in which the gas sensor has a cavity. To create the cavity on the side of the bottom electrode 125, similar approaches can be used as the cavities of current pressure sensors and/or MEMs microphones. A sacrificial oxide layer supports the build-up of the layered structure (with the necessary barrier layers for etch-stops (not shown) and at the end the cavity is etched by means of controlled vapor-HF etching (preferred) or wet-etching. As the Nafion film is highly fluorinated, it is expected it can withstand (low concentration) vapor-HF etching.

The Nafion film is preferably spin-coated and patterned in a Nafion cavity, to provide a sufficiently smooth surface for the top metal electrode. The Nafion film can be dry etched with help of resist. The top metal electrode should also be patterned similarly as in CMOS standard manufacturing methods.

Both electrodes 120, 125 generally withstand ambient atmosphere during lifetime and are preferably made of platinum. However, use of other metals such as gold, tungsten, alloys, or conductive polymers may be suitable as well. Alternatively thin, conductive, corrosion protective layers can also be used between the electrode and the Nafion film.

Alternatively, also porous electrodes can be used through which the analyze gas and reactants are able to penetrate.

In a final process integration step the sensor top electrodes are passivated and bond pads are opened as well as the sensing spot above the cavity, leaving the Nafion film (with its top-electrodes), a sensing area, exposed to the outside environment.

A film-assisted molding process may be used to package the chip and leave only the sensor area exposed to the outside environment.

The manufacturing steps above (of FIG. 6) are summarized as follows:

In step 1 (S1): Oxide is deposited. This is partly a sacrificial oxide layer supporting the build-up of the layered structure.

In step 2 (S2): Contacts are formed to the electrical contacts below on the ASIC wafer.

In step 3 (S3): Bottom electrodes (on the underneath side of the electrochemical film) are deposited In step 4 (S4): The bottom electrodes are patterned and cleaned In step 5 (S5): Oxide gapfill and planarize. Outside the Nafion film sensing area, the inter-metal dielectric spacing for the via-connections to the top electrodes is formed. This oxide insulates the via-connections. This step also prevents the bottom electrodes sinking into the Nafion film In step 6 (S6): Further oxide is deposited and contact formation. The cavity is formed by etching.

In step 7 (S7): The electrochemical (e.g., Nafion) film is deposited. The Nafion film is preferably spin-coated and patterned in a Nafion cavity, to provide a sufficiently smooth surface for the top metal electrode. The Nafion film can be dry etched with help of resist.

In step 8 (S8): The top electrodes are deposited. These electrodes are on an opposite surface of the electrochemical film to the bottom electrodes.

In step 9 (S9): The top electrodes are patterned.

In step 10 (S10): Cleaning steps including etching the cavity: This includes patterning of a hole, hole etching, and vapor HF release of the cavity underneath the bottom electrode. To enable the etch selectivity of the vapor HF step, several etch stop layers may be integrated in the manufacturing process. The etch stop layers define the cavity.

In step 11 (S11): A passivation layer is formed on the structure with an opening to sensor. This leaves the Nafion film exposed to the outside environment.

In step 12 (S12): Bondpad opening. The bondpads of the ASIC are reached through using separate bondpad etching.

Figure 7:
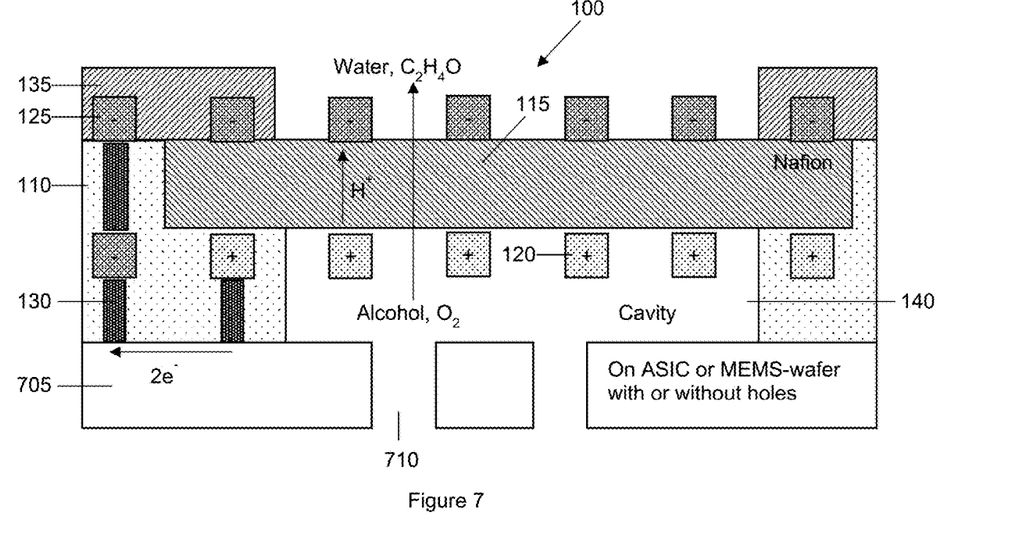
FIG. 7 illustrates a cross-sectional view of a gas sensor according to one embodiment of the present disclosure.

FIG. 7 illustrates a cross-sectional view of an alternative gas sensor according to one embodiment of the present disclosure. Many features of this embodiment are the same as those shown in FIG. 4 and therefore carry the same reference numerals. In this embodiment, the polarities of the electrodes 120, 125 are reversed with respect to the electrodes shown in FIG. 4. Furthermore, in this embodiment, the sensor device 100 is made with holes 710 in the supporting ASIC wafer 705 to improve the access and speed of the air flow. This allows air to flow from underneath the electrochemical (e.g., Nafion) film 115. The presence of holes on the bottom of the device reduces the functional CMOS area of the ASIC 705.

Figure 8:
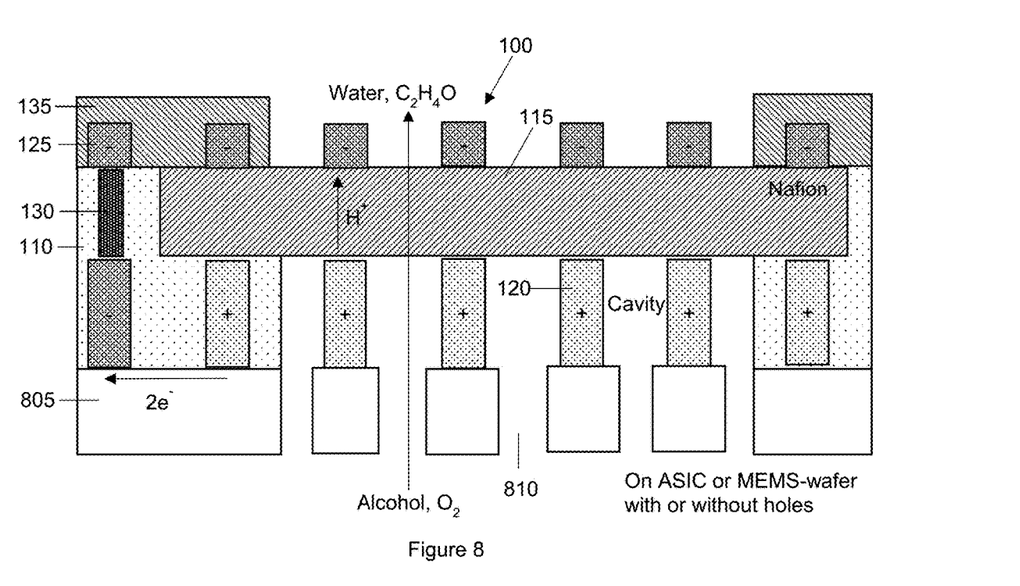
FIG. 8 illustrates a cross-sectional view of an alternative gas sensor according to one embodiment of the present disclosure.

FIG. 8 illustrates a cross-sectional view of an alternative gas sensor according to one embodiment of the present disclosure. Many of the features of this embodiment are the same as those shown in FIG. 4 and therefore carry the same reference numerals. Similar to the embodiment of FIG. 7, in this embodiment the polarities are reversed, and the ASIC wafer 805 has holes 810 to improve air flow. In this embodiment the height of the bottom electrode 120 and the cavity height are increased for providing an improved support to the electrochemical (e.g., Nafion) film 115. The heights may also be decreased.

Figure 9:
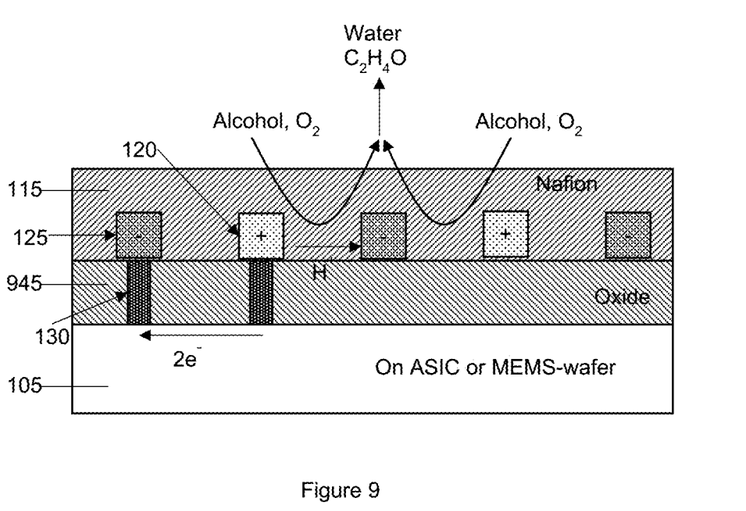
FIG. 9 illustrates a cross-sectional view of an alternative gas sensor according to one embodiment of the present disclosure.

FIG. 9 illustrates a cross-sectional view of an alternative gas sensor according to one embodiment of the present disclosure. Many of the features of this embodiment are the same as those shown in FIG. 4 and therefore carry the same reference numerals. In this embodiment there is no cavity underneath the electrochemical film 115. This provides an easier variant to integrate the alcohol sensors on top of a carrier wafer (ASIC of MEMS-wafer) 105. The Nafion film 115 is thin enough to allow the in-diffusion of the breath-alcohol to the electrode 120 (anode), where the electrochemical reaction starts.

The electrodes 120, 125 are formed in a comb and/or meander structure, such that the air flows over the surface of the electrochemical film 115.

A comb (meander) electrode structure 120, 125 is patterned on top of the planarized passivation layer 945 of a carrier wafer 105 (i.e. an ASIC wafer). As a final step the Nafion film 115 is spin-coated, cured, and patterned as a last step. In this way the alcohol sensor film is minimally affected, leaving its properties best preserved. In this embodiment without a cavity, the analyte enters on one side, it is converted, and the reaction products leave at the same side of the Nafion film 115. This embodiment does not require the gas to be measured going through the Nafion film 115 (e.g., electrolyte). This geometry makes the total semiconductor processing of the fuel cell easier. In this embodiment this is the smallest distance between the sensor and the ASIC. This improves speed, performance, and accuracy of the sensor. As there is no cavity in this embodiment, the integration of this sensor is easier. This allows a more cost-effective sensor.

Figure 10:
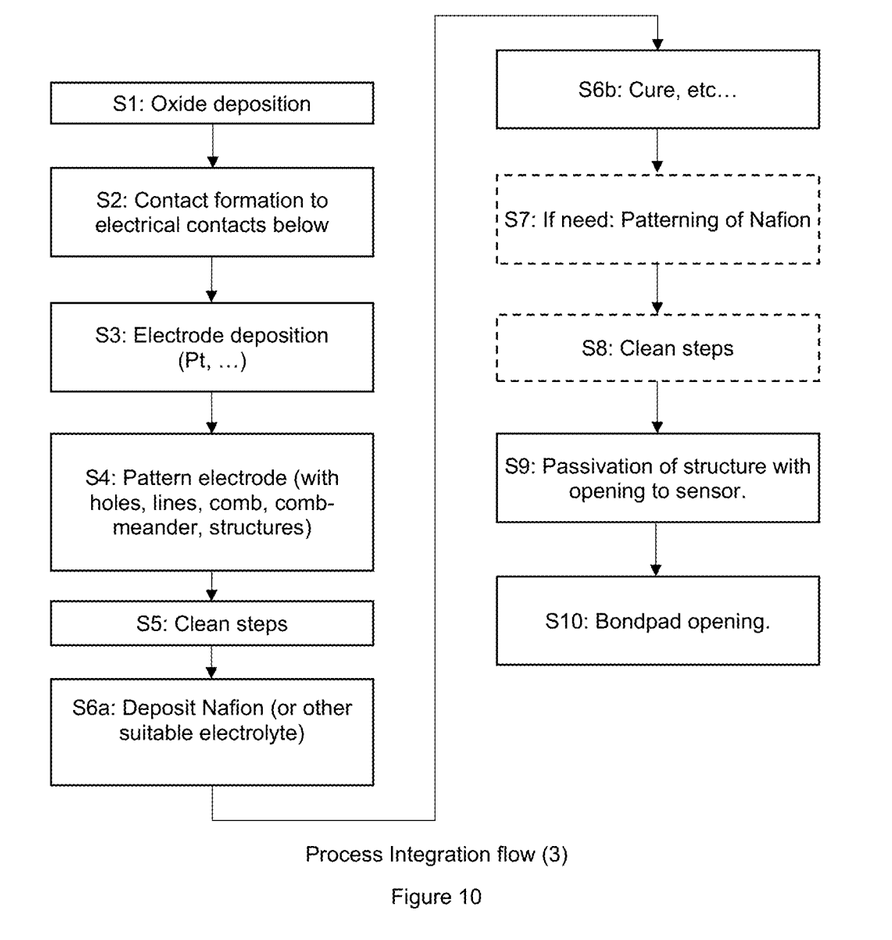
FIG. 10 illustrates an exemplary flow diagram outlining an alternative manufacturing method of a gas sensor according to one embodiment of the present disclosure.

FIG. 10 illustrates an exemplary flow diagram outlining an alternative manufacturing method of a gas sensor according to one embodiment of the present disclosure. This method illustrates the manufacturing process of a sensor without a cavity portion, starting on top of an ASIC. The starting step S1: can also be the passivation layer of the ASIC. The manufacturing steps of FIG. 10 are similar to those of FIG. 6 however the electrodes are all deposited in step 3 (S3). In step 6 (S6), the deposition of the Nafion film can be done using various techniques: spin coating, spray coating, drop coating, etc. This may need to be cured. In step 7 (S7), the Nafion film is patterned if necessary. Patterning of the Nafion film can be done by applying resist, illuminating the pattern and dry or wet etching and cleaning, or when the Nafion film is made sensitive by adding photosensitive attributes, then the film can be directly illuminated and developed and wet cleaned. In one example, this can be done by mixing photosensitive polymers in the Nafion-polymer chain. In some embodiments patterning of the Nafion film may not be needed.

Figure 11:
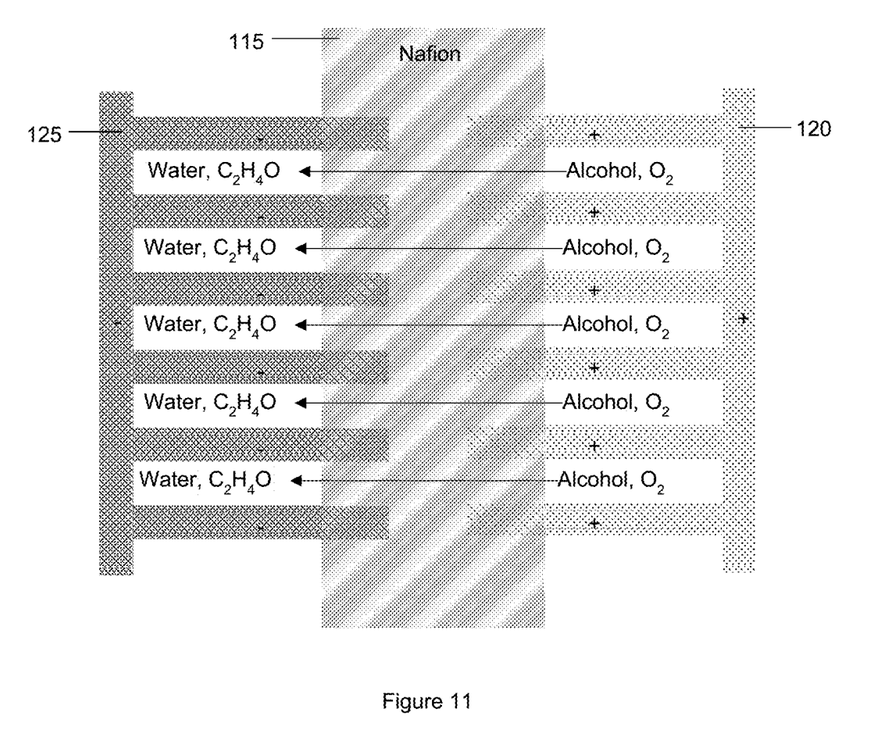
FIG. 11 illustrates a top view of an alternative gas sensor according to one embodiment of the present disclosure.

FIG. 11 illustrates a top view of an alternative gas sensor according to one embodiment of the present disclosure. The breath/air flow goes over the surface of the sensor in a direction substantially parallel to the surface of the sensor. The electrodes 120, 125 have a comb or meander shape as described in FIG. 9. Several geometries are possible to enable the alcohol sensing effect. In this geometry the electrodes 120, 125 have a comb shape, however are not interdigitated. The gas to be sensed flows across the film from the positive electrodes 120 to the negative electrodes 125.

Figure 12:
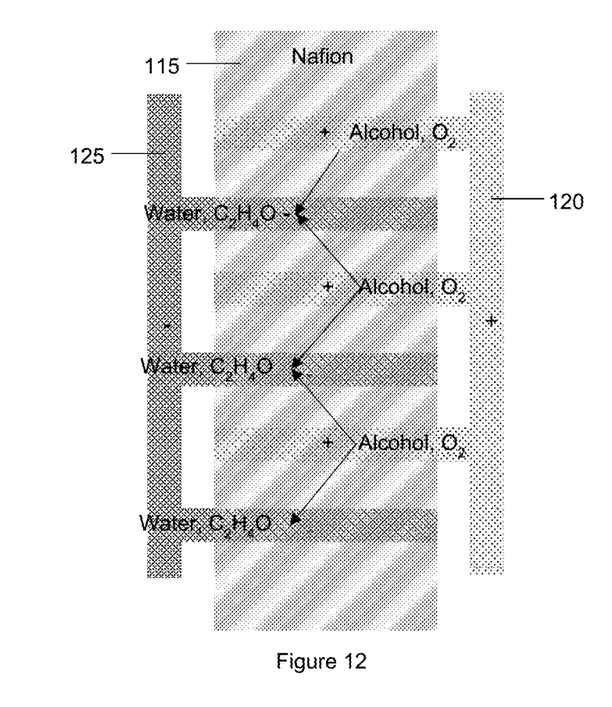
FIG. 12 illustrates a top view of an alternative gas sensor according to one embodiment of the present disclosure.

FIG. 12 illustrates a top view of an alternative gas sensor according to one embodiment of the present disclosure. This top view shows an alternative interdigitated geometry of the electrodes 120, 125 of FIG. 11. Similarly to FIG. 11, the electrodes 120, 125 have a comb shape, however they are interdigitated. This reduces the size of the gas sensor. The gas to be sensed flows across the surface of the electrochemical film 115 from the positive electrodes 120 to the negative electrodes 125.

Figure 13:
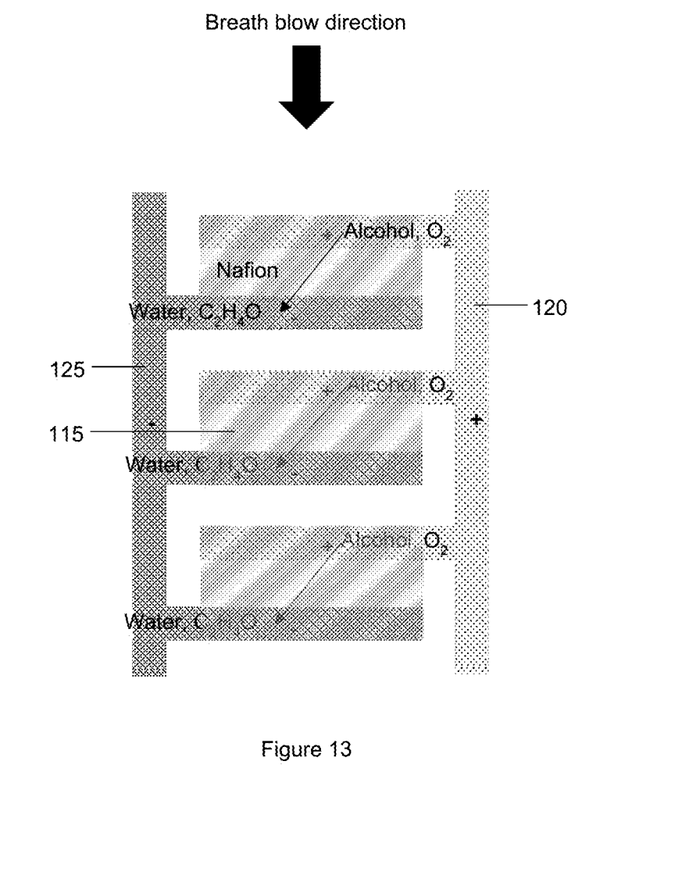
FIG. 13 illustrates a top view of an alternative gas sensor according to one embodiment of the present disclosure.

FIG. 13 illustrates a top view of an alternative gas sensor according to one embodiment of the present disclosure. This top view shows an alternative geometry of the electrodes of FIGS. 11 and 12. Similarly to FIG. 12, the electrodes 120, 125 have a comb shape, and are interdigitated. This reduces the size of the gas sensor. In this embodiment the electrochemical film 115 is patterned such that it is formed of discrete islands or portions. The gas to be sensed flows from the positive electrode 120 to the negative electrode 125 within each electrochemical film portion. The direction of breath blow shown in this embodiment is perpendicular to that shown in FIG. 11. As in the other embodiments, the reaction direction is given by the polarity of the electrodes and the direction between electrodes of opposite polarities.

Although the description above refers to the use of Nafion as the electrochemical film, it will be understood that other types of suitable electrochemical (fuel cell) films can be used in the present disclosure, for example, hydrocarbon backbones, composite membranes (including grafted membranes, organic and inorganic nanocomposites, and Nafion based composites) and blended membranes. For example, other solid electrolytes that could be used include yttria-stabilized zirconia, beta-alumina, fluoride ion conductors such as lanthanum trifluoride, iodides such as silver iodide, silver sulfide, lead(II) chloride, perovskite ceramics such as strontium titanate and strontium stannate, polyacrylamides and agar, among others.

The skilled person will understand that in the preceding description and appended claims, positional terms such as 'top', 'bottom', 'above', 'overlap', 'under', 'lateral', etc. are made with reference to conceptual illustrations of an apparatus, such as those showing standard cross-sectional perspectives and those shown in the appended drawings. These terms are used for ease of reference but are not intended to be of limiting nature. These terms are therefore to be understood as referring to a device when in an orientation as shown in the accompanying drawings.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

The invention claimed is:

1. A gas sensor comprising:
   an electrochemical film;
   a first plurality of electrodes and a second plurality of electrodes coupled with the electrochemical film, wherein the first plurality of electrodes are located on a first surface of the electrochemical film, and wherein the second plurality of electrodes are located on a second surface of the electrochemical film, and wherein the first surface of the electrochemical film and the second surface of the electrochemical film are opposite surfaces;
   a semiconductor wafer coupled with the first plurality of electrodes and the second plurality of electrodes, wherein the semiconductor wafer is an application specific integrated circuit complementary metal oxide semiconductor (ASIC CMOS) wafer; and
   a dielectric layer coupled between the electrochemical film and the semiconductor wafer, and wherein the dielectric layer comprises an etched cavity portion such that the etched cavity portion extends underneath at least some of either the first plurality of electrodes or the second plurality of electrodes and separates the at least some of the first plurality of electrodes or the second plurality of electrodes from the ASIC CMOS wafer, and
   wherein the dielectric layer is monolithically integrated on to the ASIC CMOS wafer;
   wherein the gas sensor is configured such that a gas to be sensed passes through the electrochemical film in a transverse direction from the first surface to the second surface.

2. The gas sensor of claim 1, wherein the ASIC CMOS wafer comprises laterally spaced structures having holes between them.

3. The gas sensor of claim 1, further comprising a passivation layer between the electrochemical film and the semiconductor wafer.

4. The gas sensor of claim 1, wherein the gas sensor is configured to be an alcohol sensor.

5. The gas sensor of claim 1, wherein the electrochemical film is a solid electrolyte.

6. The gas sensor of claim 1, wherein the electrochemical film and the first plurality of electrodes and the second plurality of electrodes form an electrochemical fuel cell.

7. The gas sensor of claim 1, wherein the first plurality of electrodes and the second plurality of electrodes comprise a porous material such that a gas to be sensed and/or reactants are able to pass through the first plurality of electrodes and the second plurality of electrodes.

8. The gas sensor of claim 1, wherein the first plurality of electrodes and the second plurality of electrodes form a comb or meander structure.

\* \* \* \* \*